United States Patent [19]

Abe

[11] Patent Number: 4,782,148

[45] Date of Patent: Nov. 1, 1988

[54] METHOD FOR PRODUCTION OF PERFLUORO N-(VINYL)AMINES

[75] Inventor: Takashi Abe, Kasugai, Japan

[73] Assignees: Agency of Industrial Science & Technology; Ministry of International Trade & Industry, both of Tokyo, Japan

[21] Appl. No.: 886,608

[22] Filed: Jul. 18, 1986

[30] Foreign Application Priority Data

Jul. 23, 1985 [JP] Japan .................................. 60-162631
Jul. 23, 1985 [JP] Japan .................................. 60-162632
Jul. 23, 1985 [JP] Japan .................................. 60-162633

[51] Int. Cl.$^4$ ..................... C07C 87/26; C07D 265/30; C07D 211/68; C07D 241/02
[52] U.S. Cl. .................................. 540/484; 544/106; 544/358; 548/400; 564/509; 564/510
[58] Field of Search ................ 548/400, 578; 564/509, 564/510; 540/484; 544/409, 410, 106, 358

[56] References Cited

U.S. PATENT DOCUMENTS 1,065,160  6/1913  Merling et al. ...................... 564/509
3,235,561  2/1966  Haszeldine et al. ................. 548/400

Primary Examiner—Glennon H. Hollrah
Assistant Examiner—D. B. Springer
Attorney, Agent, or Firm—Oblon, Fisher, Spivak, McClelland & Maier

[57] ABSTRACT

A perfluoro compound containing a group of the general formula:

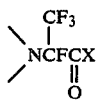

wherein X stands for a fluorine atom, perfluoro-alkoxy groups, or —OM where M stands for an alkali metal ion or an alkaline earth earth ion and having connected to the aforementioned group a perfluoro-alkyl group possessing a total of 2 to 6 carbon atoms in the trunk carbon chain thereof is subjected to a temperature in the range of 100° to 500° C. to produce a perfluoro-(N-vinylamine) compound now containing the aforementioned group as converted into the formula:

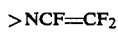

5 Claims, No Drawings

METHOD FOR PRODUCTION OF PERFLUORO N-(VINYL)AMINES

FIELD OF THE INVENTION AND RELATED ART STATEMENT

This invention relates to a method for the production of perfluoro-(N-vinylamine) compounds. More particularly, this invention relates to a method for efficient production of perfluoro-(N-vinylamine) compounds useful as raw materials for the manufacture of synthetic intermediates for such fluorine-containing products as surfactants, dyes, agricultural pesticides, and pharmaceutical chemicals and as raw materials for the manufacture of fluorine-containing plastics, by using readily available raw materials.

In the perfluoro-(N-vinylamine), a perfluoro-alkyl amino group is bonded to one of the carbon atoms in the double bond. By using this compound as an intermediate raw material, various useful compounds containing the aforementioned perfluoro-alkyl amino group can be produced. Further, by copolymerizing the compound with other fluoro-olefins, polymers incorporating therein the perfluoro-alkyl amino group, possessing lowered degrees of crystallinity, and excelling in mechanical properties can be obtained. The perfluoro-(N-vinylamine) described above is an extremely useful compound as a raw material for synthetic intermediates and for flouroine-containing plastics.

Since perfluoro-(N-vinylamine) compounds generally are not easily produced, however, perfluoro-(N,N-dimethylvinylamine) $(CF_3)_2NCF=CF_2$ (U.S. Pat. No. 3,311,599), perfluoro(N-vinylpiperidine):

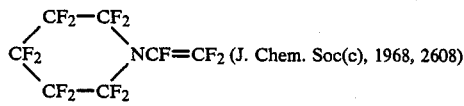

(J. Chem. Soc(c), 1968, 2608)

and perfluoro-(N-vinylmorpholine):

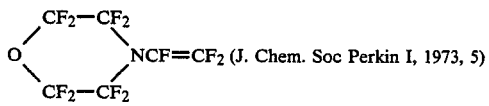

(J. Chem. Soc Perkin I, 1973, 5)

have been barely known to the art. These compounds are invariably synthesized through two steps of operation. As starting materials, they use perfluoro-alkyl nitrogen radical donating compounds, N-chlorobis(trifluoromethyl)amine, perfluoro-(N-fluoropiperidine), and perfluoro-(N-fluoromorpholine), respectively. These starting materials are first subjected to a free radical reaction with a proper fluorine-containing olefin to form 1:1 adducts. Then, these adducts are subjected to a reaction for the removal of HCl, in the case of $(CF_3)_2NCF=CF_2$ or to thermal decomposition, in the case of

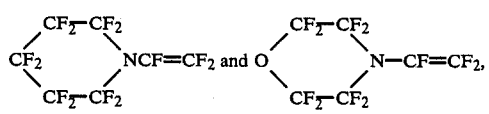

to produce unsaturated bonds.

For example, perfluoro-(N,N-dimethylvinylamine) represented by the formula:

$$(CF_3)_2NCF=CF_2 \qquad (I)$$

has heretofore been produced through the two steps of operation shown by the following formulas (U.S. Pat. No. 3,311,599). In the first step, in accordance with the following reaction formula, N-chlorobis-(trifluoromethyl)amine and trifluoroethylene are subjected to a radical reaction as exposed to an ultraviolet light to give rise to a 1:1 adduct.

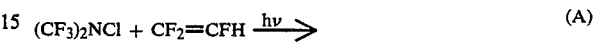

$$(CF_3)_2NCFHCF_2Cl + (CF_3)_2NCF_2CFHCl$$
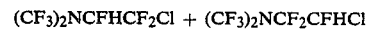

Then, in the second step, the 1:1 adduct obtained in the preceding step is subjected to a reaction for the removal of hydrogen chloride in the presence of powdered potassium hydroxide to produce perfluoro-(N,N-dimethylvinylamine) (I) as shown by the following reaction formula:

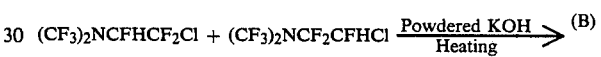

$$(CF_3)_2NCF=CF_2 + (CF_3)_2NCF=CFCl$$
(I)

In accordance with this method, however, the reaction of the formula (A) disadvantages in that, for example, the overall conversion ratio is poor (50%) and a fairly large amount of N-(2-chloro-1,1,2-trifluoroethyl)-bis-(trifluoromethyl)amine (IV), which is isomer of compound (III), is by-produced (ratio of compounds (III): (IV) produced=84:14 as determined on the peak areas of gas chromatograph) besides producing N-(2-chloro-2,2,1-trifluoroethyl)-bis-(trifluoromethyl)amine (III) as aimed at. Also in the reaction of the formula (B) for the removal of hydrogen chloride, the conversion ratio is low (55 to 60%).

Further, N-chlorobis-(trifluoromethyl)amine (II) is obtained by the reaction of bis-(trifluoromethyl)amine, $(CF_3)_2NH$, with chlorine (U.S. Pat. No. 3,052,723). The production of bis-(trifluoromethyl)amine has a disadvantage in that the procedure involved is complicated and necessitates numerous reagents and various devices and consumes much time.

In the synthesis of perfluoro-N-(vinyl)piperidine which is a perfluoro-N-(vinyl)cyclic amine, for example, perfluoro-(N-fluoropiperidine) and perfluorocyclobutene are subjected to a radical reaction as exposed to an ultraviolet light to produce a 1:1 adduct (V) in the first step of operation.

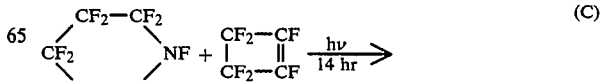

-continued

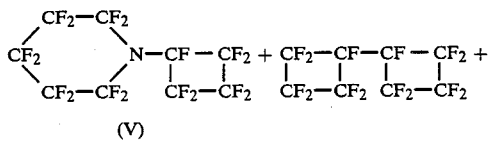

(V)

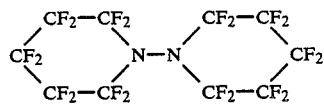

By thermally decomposing perfluoro-N-(cyclobutyl)piperidine (V) consequently obtained under reduced pessure, perfluoro-N-(vinyl)piperidine aimed at is produced.

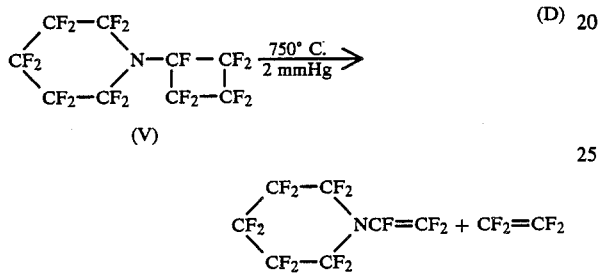

This method, however, suffers from a disadvantage that the reaction of the formula (C) produces the 1:1 adduct in a poor yield (44%) and consumes much time (14 hours of exposure time).

An attempt at applying this method to the production of some other perfluoro-N-(vinyl)-cyclic amine has been futile because no other N-(fluoro)perfluoro-cyclic amine than perfluoro-(N-fluoropiperidine) and perfluoro-(N-fluoromorpholin) has beenn available as a perfluoro-cyclo-alkyl nitrogen radical donor.

Thus, the conventional methods for the production of perfluoro-(N-vinylamines) have entailed various drawbacks and cannot rightly be called commercial manufacturing processes.

OBJECT AND SUMMARY OF THE INVENTION

An object of this invention is to provide a commercially practicable method for producing perfluoro(N-vinylamine) compounds useful as synthetic intermediates and as monomers for the manufacture of fluorine-containing polymers from readily available raw materials by a simple procedure in high yields.

The inventor continued a study for realizing the aforesaid object and has completed the present invention as a result.

To be specific, this invention is directed to a method for the production of a perfluoro(N-vinylamine) compound containing the following group:

>NCF=CF$_2$ (VII)

which method comprises subjecting to a temperature in the range of 100° to 500 ° C. a perfluoro compound containing a group represented by the following general formula:

(wherein X stands for one member selected from the class consisting of a fluorine atom, perfluoro-alkoxy groups, and —OM where M stands for a monovalent alkali metal ion or alkaline earth metal ion) and having joined to the aforementioned group a perfluoro-alkyl group possessing a total of 2 to 6 carbon atoms in the trunk carbon chain thereof.

DETAILED DESCRIPTION OF THE PREFERRED EMBODIMENTS

In all the perfluoro-(N-vinylamine) compounds that can be obtained by the method of this invention, those other than perfluoro-(N,N-dimethylamine), perfluoro-(N-vinylpiperidine), and perfluoro-(N-vinylmorpholine) are novel compounds never reported in literature to date.

As concrete examples of perfluoro-alkyl amino groups in the perfluoro compounds usable as the raw materials in the method of this invention, those of the following formulas may be cited (wherein n and m each stand for an integer of the value of 1 to 5).

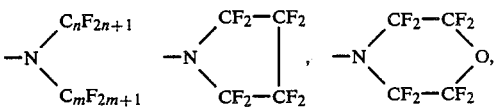

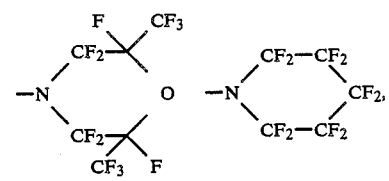

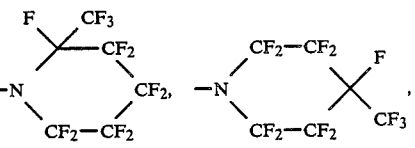

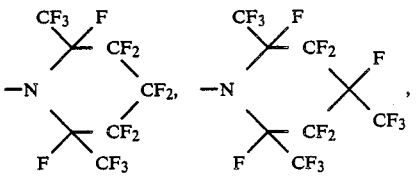

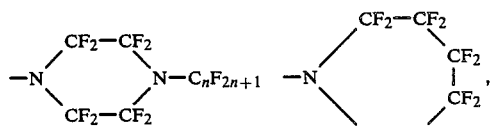

Generally, the perfluoro compounds as raw materials for this invention can be easily obtained by subjecting esters or halides of 2-dialkyl-amino-propionic acids to electrolytic fluorination in hydrogen fluoride. When a methyl ester is fluorinated, for example, this reaction produces perfluoro-(2-alkylaminopropionyl fluoride) as aimed at in combination with a small amount of perfluoro(methyl 2-alkylaminopropionate) as a by-product. The latter product can also be used as the raw material.

The metal salt of perfluoro-(2-alkylaminopropionic acid) is obtained by allowing the hydroxide of an alkali metal or an alkaline earth metal to react upon the perfluoro-(2-alkylaminopropionyl fluoride) and perfluoro-(methyl 2-alkylaminopropionate) produced as described above. As the perfluoro-compounds which are raw materials for the manufacture of perfluoro-(N,N-divinylpiperadine), perfluoro-(piperadine-N,N'-di-α-propionyl fluorides), perfluoro-(dimethyl piperadine-N,N'-di-α-propionates), and the dialkali salts and alkaline earth salts of perfluoro-(piperadine-N,N'-di-α-propionic acids) are used. Preferably, they are sodium and potassium salts.

The aforementioned perfluoro-(piperazine-N,N'-di-α-propionic acid fluoride), for example, can be easily obtained by subjecting a reactive derivative, preferably dimethyl ester, of piperazine-N,N'-di-α-propionic acid to electrolytic fluorination in liquid hydrogen fluoride. The electrolytic fluorination of dimethyl ester yields a small amount of perfluoro-(dimethyl piperazine-N,N'-di-α-propionates) as a by-product besides perfluoro-(piperazine-N,N'-di-α-propionyl fluorides). This by-product can also be used as a raw material for perfluoro-(N,N'-divinyl piperazine).

The metal salt of perfluoro-(piperazine-N,N'-di-α-propionic acids) are obtained by allowing the hydroxides of alkali metal or alkaline earth metal salts to react on the perfluoro-(piperazine-N,N'-di-α-propionic acid fluorides) and perfluoro-(dimethyl piperazine-N,N'-di-α-propionate) produced as described above.

The method of this invention consists simply in subjecting a perfluoro compound given as a raw material to a temperature in the range of 100° to 500° C.

In terms of the ease with which the thermal decomposition proceeds, perfluoro-(2-alkylaminopropionyl fluoride), perfluoro-(methyl 2-alkylaminopropionate), sodium salt of perfluoro-(2-alkylaminopropionic acid), and potassium salt of perfluoro-(2-alkylamino propionic acid) prove particularly desirable among the available raw materials.

The temperature of the thermal decomposition is selected in the range of 100° to 500° C., preferably in the range of 100° to 300° C. If this temperature exceeds the upper limit, the reaction tends to entail such undesirable secondary reactions as decomposition. If the temperature is lower than the lower limit, the conversion ratio of the reaction is low.

The reaction time in this case falls in the range of 10 seconds to two hours, though it is affected by the reaction temperature. The reaction time shortens as the temperature of treatment increases. It lengthens as the temperature of treatment decreases.

In this reaction of thermal decomposition, the reaction pressure does not constitute a significant factor. Although the reaction can be carried out under reduced pressure, under atmospheric pressure, or under an increased pressure. Reaction conducted under atmospheric pressure of under reduced pressure proves desirable because the recovery of the reaction product is attained relatively easily. Depending on the manner of carrying out the reaction, the thermal decomposition may be conducted using as a diluent such an inert gas as nitrogen, helium, argon, or carbon dioxide or such a non-protonic liquid compound as a polyester. In this case, the ratio of dilution is desired not to exceed 100 times the original amount.

Further in this thermal decomposition, it is important that all substances used should contain no water.

In the method of the present invention, when perfluoro-(2-alkylaminopropionyl fluoride) and perfluoro-(methyl 2-alkylaminopropionate) are used as raw materials, the reaction of thermal decomposition is desired to be carried out in the presence of a metal salt or a metal oxide. In this case, the desired perfluoro-(N-vinylamine) compounds are obtained by carrying out the reaction of the thermal decomposition while continuously feeding the raw materials to a packed layer of the metal salt or metal oxide kept at a prescribed temperature. Although the material for the reactor to be used for the thermal decomposition is not specifically limited, generally a reactor made of stainless steel or hastelloy is adopted. The form of the aforementioned packed layer is not specifically defined. The packed layer may be in the form of a fixed bed, a moving bed, or a fluidized bed.

As concrete examples of the aforementioned metal salt, there may be cited sodium carbonate, potassium carbonate, lithium carbonate, sodium phosphate, potassium phosphate, barium carbonate, calcium carbonate, magnesium carbonate, potassium sulfate, and sodium sulfate. As examples of the metal oxide, zinc oxide and cadmium oxide may be cited. Among the metal salts enumerated above, such solid bases as sodium carbonate and potassium carbonate prove particularly desirable because they are capable of decomposing the noxious $COF_2$ which occurs during the thermal decomposition.

Typical examples of perfluoro compounds as raw materials and perfluoro-(N-vinylamine) compounds as products by the method of the present invention are shown below.

| Perfluoro compounds | Perfluoro-(N—vinylamine) compounds |
|---|---|
| $(CF_3)_2NCFCX(=O)$ with $CF_3$ | $(CF_3)_2NCF=CF_2$ |
| $(CF_2)_2\!\!-\!\!(CF_2)_2$ ring $NCFCX(=O)$ with $CF_3$ | $(CF_2)_2\!\!-\!\!(CF_2)_2$ ring $NCF=CF_2$ |
| $CF_2\!-\!CF_2$, $CF_2$, $CF_2\!-\!CF_2$ ring $NCFCX(=O)$ with $CF_3$ | $CF_2\!-\!CF_2$, $CF_2$, $CF_2\!-\!CF_2$ ring $NCF=CF_2$ |
| $CF_2\!-\!CF_2$, $O$, $CF_2\!-\!CF_2$ ring $NCFCX(=O)$ with $CF_3$ | $CF_2\!-\!CF_2$, $O$, $CF_2\!-\!CF_2$ ring $NCF=CF_2$ |
| $CF_2\!-\!CF_2$, $C_nH_{2n+1}$, $CF_2\!-\!CF_2$ ring $NCFCX(=O)$ with $CF_3$ | $CF_2\!-\!CF_2$, $C_nH_{2n+1}$, $CF_2\!-\!CF_2$ ring $NCF=CF_2$ |

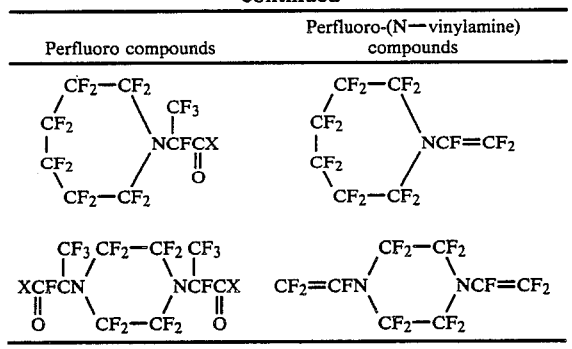

The method of the present invention enables the perfluoro-(N-vinylamine) compounds aimed at to be obtained in high yields by a very simple procedure from readily available raw materials. Thus, this is an advantageous commercial method for the manufacture of perfluoro-(N-vinylamine) compounds.

Further, from the economic point of view, the perfluoro-(N-vinylamine) compounds to be obtained by the method of this invention are highly valuable as synthetic intermediates for the manufacture of such fluorine-containing products as surfactants, dyes, agricultural pesticides, and pharmaceutical chemicals, and raw materials for the production of fluorine-containing plastics.

Now, the present invention will be described more specifically below with reference to working examples. It should be noted, however, that this invention is not limited in any sense by these working examples.

EXAMPLE 1

The product obtained by electrolytic fluorination of methyl 2-dimethylaminopropionate was distilled to expel the greater part of low-boiling compounds. The residual crude product was used as a raw material. The perfluoro-(2-dimethylaminopropionyl fluoride) content of the crude product was 69.5% by weight.

First in a three-neck flask having an inner volume of 200 ml and provided with a reflux condenser and a dropping funnel, 20.8 g of the aforementioned crude product containing 14.5 g of perfluoro-(2-dimethylaminopropionyl fluoride), 30 ml of water, and phenolphthalein added thereto as an indicator where magnetically stirred. To the stirred mixture, a concentrated aqueous potassium hydroxide solution was added dropwise as cooled with ice until the resulting mixture showed alkalinity.

Then, the reaction mixture consequently formed was transferred into an eggplant type flask having an inner volume of 200 ml and, by the use of a rotary evaporator, heated to 50° C. and then, with an aspirator, vacuumized to expel water. Consequently, there ensued precipitation of a white solid substance. The reaction system was further retained at 50° C. for about 8 hours and then dried in a vacuum.

The white solid substance obtained in the flask as described above was comminuted. Through a gas tube connected to the top of the flask, helium gas was fed into the flask at a flow rate of 80 ml/min. At the same time, the flask was heated over an oil bath to elevate the temperature slowly from 150° C. to 190° C. over a period of 30 minutes. The content of the flask was left standing at the elevated temperature for one hour to effect thermal decomposition. The product of the thermal decomposition was condensed and collected in a trap kept cooled at −78° C. Thus, a total of 9.5 g of fluorocarbon was collected.

The collected product, on analysis by gas chromatography, liquid phase: 1,6-bis-(1,1,12-trihydroperfluorododecyloxy)-hexane, carrier: 60 to 80 mesh Chromosorb PAW, and carrier gas: helium, IR, $^{19}$F NMR, and Mass, was found to consist mainly of perfluoro-(N,N-dimethylvinylamine) and contain N,N-bis-(trifluoromethyl)-1,1,2,2,2-tetrafluoroethylamine additionally.

The amount of perfluoro(N,N-dimethylvinylamine) thus produced was 8.9 g, representing a yield of 78.9%.

The boiling point and spectroscopic data of the perfluoro-(N,N-dimethylvinylamine) are shown in a separate table.

EXAMPLE 2

A stainless steel tube 48.0 cm in length and 2.5 cm in inside diameter provided as connected to the inlet side thereof with an instantaneous evaporator for vaporizing a raw material and a device for controlling the flow volume of a diluting gas and provided on the outlet side thereof with a low-temperature trap for condensing and collecting a reaction product was used as a horizontal type thermal decomposition reactor. In this reactor, 82.6 g of powdered anhydrous potassium carbonate was packed until it reached substantially the middle part in the horizontal level of the reactor. The opposite ends of this reactor were plugged with metallic wool. First, the reactor was kept at 200° C. and helium gas was passed therethrough at a flow rate of 50 ml/min. Then, 6.85 g of a fluorocarbon mixture containing perfluoro-(2-dimethylaminopropionyl fluoride) of a purity of 90.8% was supplied with a micrometering pump to the instantaneous evaporator over a period of 30 minutes, to be vaporized and mixed with helium gas fed in at a fixed rate. The mixed gas was introduced into the aforementioned reactor. The reaction product was condensed and collected in the trap cooled to −78° C. on the outlet side.

As the result, there was obtained 4.64 g of fluorocarbon. This fluorocarbon, on analysis by the same methods as used in Example 1, was found to contain 4.00 g of perfluoro-(N,N-dimethylvinylamine). The conversion ratio was 100% and the yield was 82.6%.

EXAMPLE 3

In the same reactor as used in Example 2, 85.4 g of powdered sodium carbonate was packed. In this apparatus, a reaction was carried out by following the procedure of Example 2, except that perfluoro-(2-dimethylaminopropionyl fluoride) of a purity of 94.1% was used as a fluorocarbon mixture and the reaction temperature was changed to 220° C.

When 5.71 g of the fluorocarbon mixture was supplied to the reactor over a period of 15 minutes to be thermally decomposed therein, 4.24 g of fluorocarbon was obtained in the cooling trap.

The fluorocarbon, on analysis by the same methods as used in Example 1, was found to contain 3.97 g of perfluoro-(N,N-dimethylvinylamine) and 0.16 g of unaltered perfluoro-(2-dimethylaminopropionyl fluoride). The conversion ratio was 97.0%. The yield of perfluoro-(N,N-dimethylvinylamine) based on the spent perfluoro-(2-dimethylaminopropionyl fluoride) was 97.8%.

EXAMPLE 4

In the same reactor as used in Example 2, 36.1 g of powdered zinc oxide was packed. In this reactor, a reaction was carried out by following the procedure of Example 2, except that a fluorocarbon mixture containing perfluoro-(2-dimethylaminopropionyl fluoride) in a purity of 94.1% was used as a raw material and the reaction temperature was changed to 300° C.

When 11.73 g of the fluorocarbon mixture was supplied to the reactor over a period of 19 minutes to be thermally decomposed thereon, 8.60 g of fluorocarbon was obtained in the cooling trap.

The fluorocarbon, on analysis by the same methods as usedin Example 1, was found to contain 1.55 g of perfluoro-(N,N-dimethylvinylamine) and 4.72 g of unaltered perfluoro-(2-dimethylaminopropionyl fluoride).

The conversion ratio was 42.8% and the yield of perfluoro-(N,N-dimethylvinylamine) based on the spent perfluoro-(2-dimethylaminopropionyl fluoride) was 42.4%.

EXAMPLE 5

In the same reactor as used in Example 2, 83.2 g of powdered anhydrous potassium carbonate was packed similarly, and a reaction was carried out by following the procedure of Example 2, except that the product (cell drainings) obtained by electrolytic fluorination of methyl 2-pyrrolidinopropionate was used in its unmodified form as a raw material. This product contained 71.4% by weight of perfluoro-(2-pyrrolidinopropionyl fluoride) and 7.5% by weight of perfluoro-(methyl 2-pyrrolidinopropionate).

When 5.12 g of the aforementioned fluorocarbon mixture containing 3.65 g of perfluoro-(2-pyrrolidinopropionyl fluoride) and 0.38 g of perfluoro-(methyl 2-pyrrolidinopropionate) was fed to the reactor and subjected therein to thermal decomposition over a period of 33 minutes, 3.39 g of fluorocarbon was obtained in the cooling trap.

This fluorocarbon, on analysis by the same methods as in Example 1, was found to consist mainly of Perfluoro-(N-vinylpyrrolidine) (2.72 g) and contain perfluoro-(N-ethylpyrrolidine) (0.67 g) as an impurity.

The conversion ratio was 100%. The yield of perfluoro-(N-vinylpyrrolidine) was 83.8% based on perfluoro-(2-pyrrolidinopropionyl fluoride) and perfluoro-(methyl 2-pyrrolidinopropionate). The boiling point and the spectroscopic data of perfluoro-(N-vinylpyrrolidine) are shown in the separate table.

EXAMPLE 6

In the same reactor as used in Example 2, 80.7 g of powdered anhydrous potassium carbonate was packed similarly, and a reaction was carried out by following the procedure of Example 2, except that perfluoro-(2-morpholinopropionyl fluoride) refined by GC was used as a raw material.

When 3.21 g of perfluoro-(2-morpholinopropionyl fluoride) was fed to the reactor and subjected therein to thermal decomposition over a period of 19 minutes, 1.85 g of fluorocarbon was obtained in the cooling trap.

This fluorocarbon, on analysis by the same methods as used in Example 1, was found to consist substantially wholly of pure perfluoro-N-(vinylmorpholine). The conversion ratio was 100% and the yield was 69.8%.

The boiling point and the spectroscopic data of perfluoro-(N-vinylmorpholine) are shown in the separate table.

EXAMPLE 7

In the same reactor as used in Example 2, 82.5 g of powdered anhydrous potassium carbonate was packed similarly, and a reaction was carried out by following the procedure of Example 2, except that perfluoro-(2-piperizinopropionyl fluoride) refined by GC was used as a raw material.

When 3.46 g of perfluoro-(2-piperizinopropionyl fluoride) was fed to the reactor and subjected therein to thermal decomposition over a period of 27 minutes, 2.81 g of fluorocarbon was obtained in the cooling trap.

This fluorocarbon, on analysis by the same methods as in Example 1, was found to consist substantially wholly of pure perfluoro-(N-vinylpiperazine). The conversion ratio was 100% and the yield was 96.8%.

The boiling point and the spectroscopic data of perfluoro-(N-vinylpiperazine) are shown in the separate table.

EXAMPLE 8

In the same reactor as used in Example 2, 84.3 g of powdered anhydrous potassium carbonate was packed similarly, and a reaction was carried out by following the procedure of Example 1, except that N-ethyl-N'-1-(fluorocarbonyl)-ethylpiperazine refined by GC was used as a raw material.

When 2.38 g of perfluoro-N-ethyl-N'-1-(fluorocarbonyl)ethyl piperazine was fed to the reactor and subjected therein to thermal decomposition over a period of 12 minutes, 1.88 g of fluorocarbon was obtained in the cooling trap.

The fluorocarbon, on analysis by the same methods as used in Example 1, was found to consist substantially wholly of pure perfluoro-(N-vinyl-N'-ethylpiperazine). The conversion ratio was 100% and the yield was 91.1%.

The boiling point and the spectroscopic data of perfluoro-(N-vinyl-N'-ethylpiperazine) are shown in the separate table.

EXAMPLE 9

In the same reactor as used in Example 2, 82.3 g of powdered anhydrous potassium carbonate was packed similarly, and a reaction was carried out by following the procedure of Example 2, except that perfluoro-(2-hexamethyleneiminopropionyl fluoride) refined by GC was used as a raw material and He flow rate was 100 ml/min.

When 4.00 g of perfluoro-(2-hexaethyleneiminopropionyl fluoride) was fed to the reactor and subjected therein to thermal decomposition over a period of 31 minutes, 2.88 g of fluorocarbon was obtained in the cooling trap.

This fluorocarbon, on analysis by the same methods as in Example 1, was found to consist substantially wholly of pure perfluoro-(N-vinylhexamethyleneimine). The conversion ratio was 100% and the yield was 84.0%.

The boilinhg point and the spectroscopic data of perfluoro-(N-vinylhexamethyleneimine) are shown in the separate table.

EXAMPLE 10

In entirely the same horizontal type thermal decomposition reactor as used in Example 2, 82.0 g of powdered anhydrous potassium carbonate was packed in entirely the same manner as in Example 2.

Then, the aforementioned reactor was kept at 200° C. and helium gas was fed thereto at a flow rate of 50 ml/min. At the same time, 2.83 g of perfluoro-N,N'-di 1-(fluorocarbonyl)-ethylpiperazine was fed by a micrometering pump to the instantaneous evaporator over 22 minutes, to be vaporized and mixed with the helium gas being introduced at a fixed rate and introduced into the aforementioned reactor. When the reaction product was condensed and collected in the trap kept at −78° C. on the outlet side of the reactor, 1.90 g of fluorocarbon was obtained.

The fluorocarbon mixture, on analysis by the same methods as in Example 1, was found to consist substantially wholly of pure perfluoro-(N,N'-divinylpiperazine). The conversion ratio was 100% and the yield was 89.9%.

The boiling point and the spectroscopic data of perfluoro-(N,N'-divinylpiperazine) are shown in the separate table.

| Example | Perfluoro-vinylamine | BP(°C.) | IR(cm⁻¹) ν(CF$_2$=CF—) | ¹⁹F NMR Chemical shift (PPM based on CFCl$_3$) | J(Hz) |
|---|---|---|---|---|---|
| 1 | 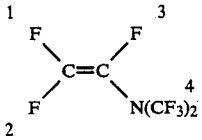 | 13.7 | 1812 | 1 −97.3<br>2 −110.9<br>3 −144.3<br>4 −58.3 | 1 − 2 = 49<br>1 − 3 = 53<br>2 − 3 = 114 |
| 5 | 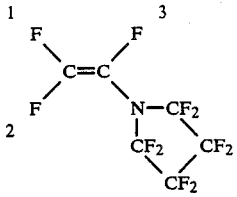 | 56.5~57.8 | 1809 | 1 −94.2<br>2 −111.1<br>3 −146.9 | 1 − 2 = 46<br>1 − 3 = 53<br>2 − 3 = 116 |
| 6 | 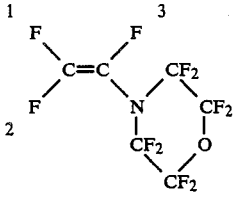 | 64.5~65.6 | 1814 | 1 −95.3<br>2 −110.4<br>3 −128.4 | 1 − 2 = 46<br>1 − 3 = 54<br>2 − 3 = 115 |
| 7 | 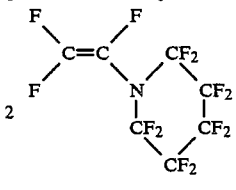 | 78.3~78.5 | 1814 | 1 −95.8<br>2 −110.3<br>3 −145.2 | 1 − 2 = 47<br>1 − 3 = 54<br>2 − 3 = 115 |
| 8 | 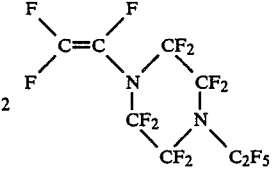 | 108.5~112.0 | 1815 | 1 −95.2<br>2 −110.4<br>3 −146.6 | 1 − 2 = 46<br>1 − 3 = 55<br>2 − 3 = 115 |
| 9 | 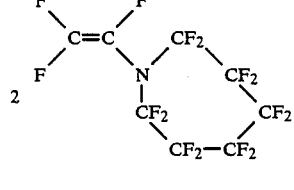 | 102.0~103.0 | 1809 | 1 −96.1<br>2 −106.1<br>3 −141.1 | 1 − 2 = 47<br>1 − 3 = 55<br>2 − 3 = 116 |

-continued

| Example | Perfluoro-vinylamine | BP(°C.) | IR(cm$^{-1}$) $\nu$(CF$_2$=CF—) | Chemical shift (PPM based on CFCl$_3$) | J(Hz) |
|---|---|---|---|---|---|
| 10 | 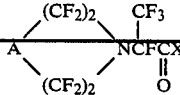 | 108.0~110 | 1814 | 1  −94.9<br>2  −110.3<br>3  −145.3 | 1 − 2 = 44<br>1 − 3 = 115 |

What is claimed is:

1. A method for the production of a perfluoro-(N-vinylamine) compound having the formula:

(CF$_3$)$_2$NCF=CF$_2$ which method comprises subjecting to a temperature in the range of 100° to 500° C. a perfluoro compound having the formula

wherein X stands for a member selected from the group consisting of a fluorine atom, a perfluoroalkoxy group, and —OM where M stands for one member selected from the group consisting of monovalent alkali metal ions and alkaline earth metal ions.

2. A method for the production of a perfluoro-(N-vinylamine) compound having the formula:

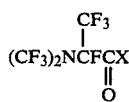

which method comprises subjecting to a temperature in the rage of 100° to 500° C. a perfluoro compound having the formula

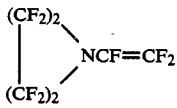

wherein X stands for a member selected from the group consisting of a fluorine atom, a perfluoroalkoxy group, and —OM where M stands for one member selected from the group consisting of monovalent alkali metal ions and alkaline earth metal ions.

3. A method for the production of a perfluoro-(N-vinylamine) compound having the formula:

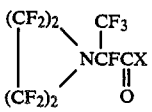

wherein A stands for a member selected from the group consisting of CF$_2$<, O<, >NC$_n$F$_{2n+1}$, where n stands for an integer from 2 to 6, which method comprises subjecting to a temperature in the range of 100° to 500° C. a perfluoro compound having the formula

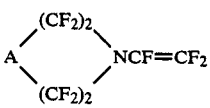

wherein A is as defined above, and X stands for a member selected from the group consisting of a fluorine atom, a perfluoroalkoxy group, and —OM where M stands for one member selected from the group consisting of monovalent alkali metal ions and alkaline earth metal ions.

4. A method for the production of a perfluoro-(N-vinylamine) compound having the formula:

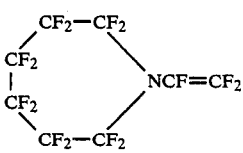

which method comprises subjecting to a temperature in the range of 100° to 500° C. a perfluoro compound having the formula

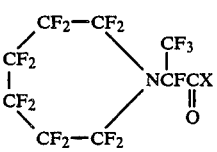

wherein X stands for a member selected from the group consisting of a fluorine atom, a perfluoroalkoxy group, and —OM where M stands for one member selected from the group consisting of monovalent alkali metal ions and alkaline earth metal ions.

5. A method for the production of a perfluoro-(N-vinylamine) compound having the formula:

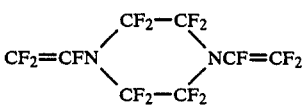

which method comprises subjecting to a temperature in the range of 100° to 500° C. a perfluoro compound having the formula

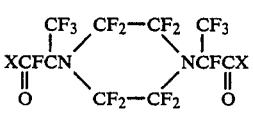

wherein X stands for a member selected from the group consisting of a fluorine atom, a perfluoroalkoxy group, and —OM where M stands for one member selected from the group consisting of monovalent alkali metal ions and alkaline earth metal ions.

* * * * *